(12) United States Patent
Forster

(10) Patent No.: US 10,896,301 B2
(45) Date of Patent: Jan. 19, 2021

(54) RFID-BASED METHODS AND SYSTEMS FOR MONITORING MEDICATION COMPLIANCE

(71) Applicant: Avery Dennison Retail Information Services, LLC, Mentor, OH (US)

(72) Inventor: Ian James Forster, Chelmsford-Essex (GB)

(73) Assignee: Avery Dennison Retail Information Services, LLC, Mentor, OH (US)

( * ) Notice: Subject to any disclaimer, the term of this patent is extended or adjusted under 35 U.S.C. 154(b) by 0 days.

(21) Appl. No.: 14/793,357

(22) Filed: Jul. 7, 2015

(65) Prior Publication Data

US 2017/0011240 A1    Jan. 12, 2017

(51) Int. Cl.
*G06K 7/10* (2006.01)
*A61J 1/03* (2006.01)
(Continued)

(52) U.S. Cl.
CPC ........ *G06K 7/10366* (2013.01); *A61B 5/4833* (2013.01); *A61J 1/035* (2013.01);
(Continued)

(58) Field of Classification Search
CPC .. A61J 1/035; A61J 2200/30; G06K 7/10366; B65D 75/327; B65D 75/367
See application file for complete search history.

(56) References Cited

U.S. PATENT DOCUMENTS

| 4,429,792 A | 2/1984 | Machbitz |
| 4,526,474 A | 7/1985 | Simon |

(Continued)

FOREIGN PATENT DOCUMENTS

| CN | 1314863 | 9/2001 |
| CN | 1395916 | 2/2003 |

(Continued)

OTHER PUBLICATIONS

International Search Report and Written Opinion dated Oct. 4, 2016 for International Application No. PCT/US2016/039720 filed Jun. 28, 2016.

(Continued)

*Primary Examiner* — Nabil H Syed

(57) ABSTRACT

Systems and methods are provided for monitoring medication compliance to allow a doctor or medical care provider to determine whether a subject is ingesting a prescribed medication at the proper times. A medication container includes at least one medication-containing cell, with a cover overlaying the cell. The medication within the cell is accessed through the cover. The medication container also includes an electrical circuit having an RFID chip electrically coupled to an antenna. The RFID chip is associated with the cover, while the antenna is configured to communicate with an RFID reader to detect whether the cell has been accessed through the cover. The RFID chip may be uncoupled from the antenna or remain coupled to the antenna upon the cell being accessed through the cover, with the antenna thereafter transmitting a signal to an RFID reader to indicate that the cell has been accessed through the cover.

22 Claims, 3 Drawing Sheets

(51) Int. Cl.
*G06F 19/00* (2018.01)
*A61B 5/00* (2006.01)
*A61J 7/04* (2006.01)

(52) U.S. Cl.
CPC ......... *G06F 19/3462* (2013.01); *A61J 7/0418* (2015.05); *A61J 7/0436* (2015.05); *A61J 2205/60* (2013.01)

(56) References Cited

U.S. PATENT DOCUMENTS

| | | | |
|---|---|---|---|
| 4,617,557 A | 10/1986 | Gordon | |
| 4,660,991 A | 4/1987 | Simon | |
| 5,181,189 A | 1/1993 | Hafner et al. | |
| 5,313,439 A | 5/1994 | Albeck | |
| 5,412,372 A | 5/1995 | Parkhurst et al. | |
| 5,642,731 A | 7/1997 | Kehr | |
| 5,836,474 A | 11/1998 | Wessberg | |
| 5,871,831 A | 2/1999 | Zeiter et al. | |
| 5,905,653 A | 5/1999 | Highham et al. | |
| 6,048,087 A | 4/2000 | Laurent et al. | |
| 6,294,999 B1 | 9/2001 | Yarin et al. | |
| 6,339,732 B1 | 1/2002 | Phoon et al. | |
| 6,411,567 B1 | 6/2002 | Niemiec et al. | |
| 6,664,887 B1 | 12/2003 | Fuchs | |
| 6,824,739 B1 | 11/2004 | Arney et al. | |
| 6,961,285 B2 | 11/2005 | Niemiec et al. | |
| 6,973,371 B1 | 12/2005 | Benouali | |
| 7,252,208 B1 | 8/2007 | Alvino et al. | |
| 7,298,343 B2 | 11/2007 | Forster et al. | |
| 7,828,147 B2 | 11/2010 | Caracciolo et al. | |
| 8,072,334 B2 | 12/2011 | Forster et al. | |
| 8,704,716 B2 | 4/2014 | Kato et al. | |
| 8,751,039 B1 | 6/2014 | Macoviak et al. | |
| 8,960,440 B1 | 2/2015 | Kronberg | |
| 9,172,130 B2 | 10/2015 | Forster | |
| 2001/0028308 A1 | 10/2001 | De La Huerga et al. | |
| 2002/0017996 A1 | 2/2002 | Niemiec et al. | |
| 2002/0111542 A1 | 8/2002 | Warkentin et al. | |
| 2003/0007421 A1* | 1/2003 | Niemiec ............... A61J 7/0481 368/10 | |
| 2003/0046563 A1 | 3/2003 | Ma et al. | |
| 2003/0063524 A1 | 4/2003 | Niemiec et al. | |
| 2003/0111479 A1 | 6/2003 | Taneja et al. | |
| 2003/0121930 A1 | 7/2003 | Layer et al. | |
| 2004/0078879 A1 | 4/2004 | Zach et al. | |
| 2005/0062238 A1 | 3/2005 | Broadfield et al. | |
| 2005/0162255 A1* | 7/2005 | Goel ................. G06K 19/0707 340/5.91 | |
| 2005/0162979 A1 | 7/2005 | Ostergaard et al. | |
| 2005/0237222 A1 | 10/2005 | Bogash et al. | |
| 2005/0241983 A1 | 11/2005 | Snyder et al. | |
| 2005/0252924 A1 | 11/2005 | Pieper et al. | |
| 2005/0256830 A1 | 11/2005 | Siegel et al. | |
| 2006/0061472 A1 | 3/2006 | Lovoi et al. | |
| 2006/0071774 A1 | 4/2006 | Brown et al. | |
| 2006/0079996 A1 | 4/2006 | Benouali | |
| 2006/0124656 A1 | 6/2006 | Fopovich, Jr. | |
| 2006/0144749 A1 | 7/2006 | Arnold et al. | |
| 2006/0202830 A1 | 9/2006 | Scharfeld et al. | |
| 2007/0018819 A1* | 1/2007 | Streeb ................... G06K 7/0008 340/572.1 | |
| 2007/0023316 A1 | 2/2007 | Coe et al. | |
| 2007/0246396 A1 | 10/2007 | Brollier | |
| 2008/0012579 A1 | 1/2008 | Kuhns et al. | |
| 2008/0223936 A1* | 9/2008 | Mickle ................ B65D 75/327 235/492 | |
| 2009/0210247 A1 | 8/2009 | Chudy et al. | |
| 2009/0218846 A1 | 9/2009 | Nguyen et al. | |
| 2009/0278626 A1 | 11/2009 | Lee | |
| 2009/0278688 A1* | 11/2009 | Tuttle ................. G06K 7/10346 340/572.2 | |
| 2009/0294521 A1 | 12/2009 | De La Huerga et al. | |
| 2009/0309704 A1* | 12/2009 | Chang ................... H04Q 9/00 340/10.1 | |
| 2010/0089791 A1 | 4/2010 | Rosenbaum et al. | |
| 2010/0094455 A1 | 4/2010 | Dehlin et al. | |
| 2010/0114367 A1 | 5/2010 | Barrett et al. | |
| 2010/0187243 A1* | 7/2010 | Layer ................... A61J 1/035 220/694 | |
| 2010/0314282 A1 | 12/2010 | Bowers | |
| 2011/0037485 A1 | 2/2011 | Kiy | |
| 2012/0003928 A1 | 1/2012 | Geboers et al. | |
| 2012/0010939 A1 | 1/2012 | Krishnamoorth et al. | |
| 2012/0056000 A1 | 3/2012 | Shores | |
| 2012/0109397 A1 | 5/2012 | Shim et al. | |
| 2012/0125994 A1 | 5/2012 | Heath et al. | |
| 2012/0156992 A1 | 6/2012 | Walker et al. | |
| 2012/0228192 A1 | 9/2012 | Niven | |
| 2012/0229279 A1 | 9/2012 | Conley et al. | |
| 2013/0044007 A1 | 2/2013 | Paavilainen et al. | |
| 2013/0195326 A1 | 8/2013 | Bear et al. | |
| 2013/0222135 A1 | 8/2013 | Stein et al. | |
| 2013/0285681 A1 | 10/2013 | Wilson et al. | |
| 2014/0039445 A1 | 2/2014 | Austin et al. | |
| 2014/0048442 A1 | 2/2014 | Maijala et al. | |
| 2014/0052467 A1 | 2/2014 | Maijala et al. | |
| 2014/0166529 A1 | 6/2014 | Fung et al. | |
| 2014/0243749 A1 | 8/2014 | Edwards et al. | |
| 2014/0262918 A1 | 9/2014 | Chu et al. | |
| 2014/0288942 A1 | 9/2014 | Blochet | |
| 2014/0340198 A1 | 11/2014 | Kawase et al. | |
| 2014/0354433 A1* | 12/2014 | Buco ................... G06Q 50/22 340/572.4 | |
| 2014/0360898 A1 | 12/2014 | Kantor et al. | |
| 2015/0032533 A1 | 1/2015 | Raab et al. | |
| 2015/0048100 A1 | 2/2015 | Dickie et al. | |
| 2015/0048102 A1 | 2/2015 | Dickie et al. | |
| 2015/0048170 A1 | 2/2015 | Forster | |
| 2015/0066204 A1 | 3/2015 | Patel et al. | |
| 2015/0274402 A1 | 10/2015 | Elliott | |
| 2015/0283036 A1 | 10/2015 | Aggarwal et al. | |
| 2015/0286852 A1* | 10/2015 | Sengstaken, Jr. .. G06K 19/0716 340/10.1 | |
| 2015/0325336 A1 | 11/2015 | Maples | |
| 2015/0339566 A1 | 11/2015 | Forster | |
| 2015/0347712 A1* | 12/2015 | Flori ................... A61J 1/035 705/28 | |
| 2015/0347713 A1 | 12/2015 | Seeger | |
| 2015/0356845 A1 | 12/2015 | Forster | |
| 2016/0019452 A1 | 1/2016 | Forster | |
| 2016/0106622 A1 | 4/2016 | Van De Wouw et al. | |
| 2016/0132661 A1 | 5/2016 | Dixit et al. | |
| 2016/0137380 A1 | 5/2016 | Kosaka | |
| 2016/0143807 A1 | 5/2016 | Ika et al. | |
| 2016/0143809 A1 | 5/2016 | Webster et al. | |
| 2016/0147976 A1 | 5/2016 | Jain | |
| 2016/0158108 A1 | 6/2016 | Gofer et al. | |
| 2016/0158109 A1 | 6/2016 | Nova et al. | |
| 2016/0367435 A1 | 12/2016 | Ahmadi | |
| 2017/0011240 A1 | 1/2017 | Forster | |
| 2017/0053095 A1 | 2/2017 | Blum et al. | |
| 2017/0165151 A1 | 6/2017 | Schmid et al. | |
| 2017/0337157 A1 | 11/2017 | Rothschild | |
| 2018/0012117 A1 | 1/2018 | Forster | |
| 2018/0042105 A1 | 2/2018 | Anderson | |
| 2018/0156756 A1 | 6/2018 | Forster | |
| 2018/0319519 A1 | 11/2018 | Stange et al. | |

FOREIGN PATENT DOCUMENTS

| | | |
|---|---|---|
| CN | 1568171 | 1/2005 |
| CN | 101309846 | 11/2008 |
| CN | 202046575 | 9/2009 |
| CN | 104135985 | 11/2014 |
| EP | 1758050 | 2/2007 |
| EP | 2026253 | 2/2009 |
| NL | 151311 | 3/1977 |
| WO | 2006002667 | 1/2006 |

(56) References Cited

FOREIGN PATENT DOCUMENTS

| WO | 2008000279 | 1/2008 |
| WO | 2009116108 | 9/2009 |

OTHER PUBLICATIONS

International Search Report dated Sep. 29, 2015 for International Application No. PCT/US2015/038763 filed Jul. 1, 2015.

International Preliminary Report on Patentability and Written Opinion dated Jan. 10, 2017 for International Application No. PCT/US2015/038763 filed Jul. 1, 2015.

International Search Report and Written Opinion dated Mar. 11, 2016 for International Application No. PCT/US2015/064888 filed Dec. 10, 2015.

International Search Report and Written Opinion dated Dec. 5, 2016 for International Application No. PCT/US2016/039714 filed Jun. 28, 2016.

International Preliminary Report on Patentability dated Jun. 13, 2017 for International Application No. PCT/US2015/064888 filed Dec. 10, 2015.

International Search Report and Written Opinion dated Sep. 28, 2017 for International Application No. PCT/US2017/041125 filed Jul. 7, 2017.

International Preliminary Report on Patentability dated Jan. 8, 2019 for international Application No. PCT/US2017/041125 filed Jul. 7, 2017.

International Preliminary Report on Patentability dated Jan. 18, 2018 issued in corresponding IA No. PCT/US2016/039714 filed Jun. 28, 2016.

International Preliminary Report on Patentability dated Jan. 9, 2018 issued in corresponding IA No. PCT/US2016/039720 filed Jun. 28, 2016.

* cited by examiner

RFID-BASED METHODS AND SYSTEMS FOR MONITORING MEDICATION COMPLIANCE

BACKGROUND

Field of the Disclosure

The present subject matter relates to monitoring the medication intake of a subject. More particularly, the present subject matter relates to monitoring the medication intake of a subject using a medication container incorporating an electrical circuit with radio frequency identification ("RFID") technology.

Description of Related Art

Frequently, a doctor or medical care provider will issue instructions to a subject to periodically ingest one or more doses of medication in the form of a pill or tablet or capsule or the like as part of a treatment regimen. Unless the subject is within a facility under the control of the doctor or medical care provider (e.g., a hospital or nursing home), it can be difficult for the doctor or medical care provider to know whether the subject is ingesting the prescribed medication at the proper times. Accordingly, it would be advantageous to provide systems and methods that allow a doctor or medical care provider to monitor the medication compliance of a subject.

SUMMARY

There are several aspects of the present subject matter, which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, a medication container is provided with at least one medication-containing cell, with a cover overlaying the cell. The medication contained within the cell is accessed through the cover. The medication container also includes an electrical circuit having a radio frequency identification ("RFID") chip associated with the cover and electrically coupled to an antenna. The antenna is configured to communicate with an RFID reader to detect whether the cell has been accessed through the cover.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 2:
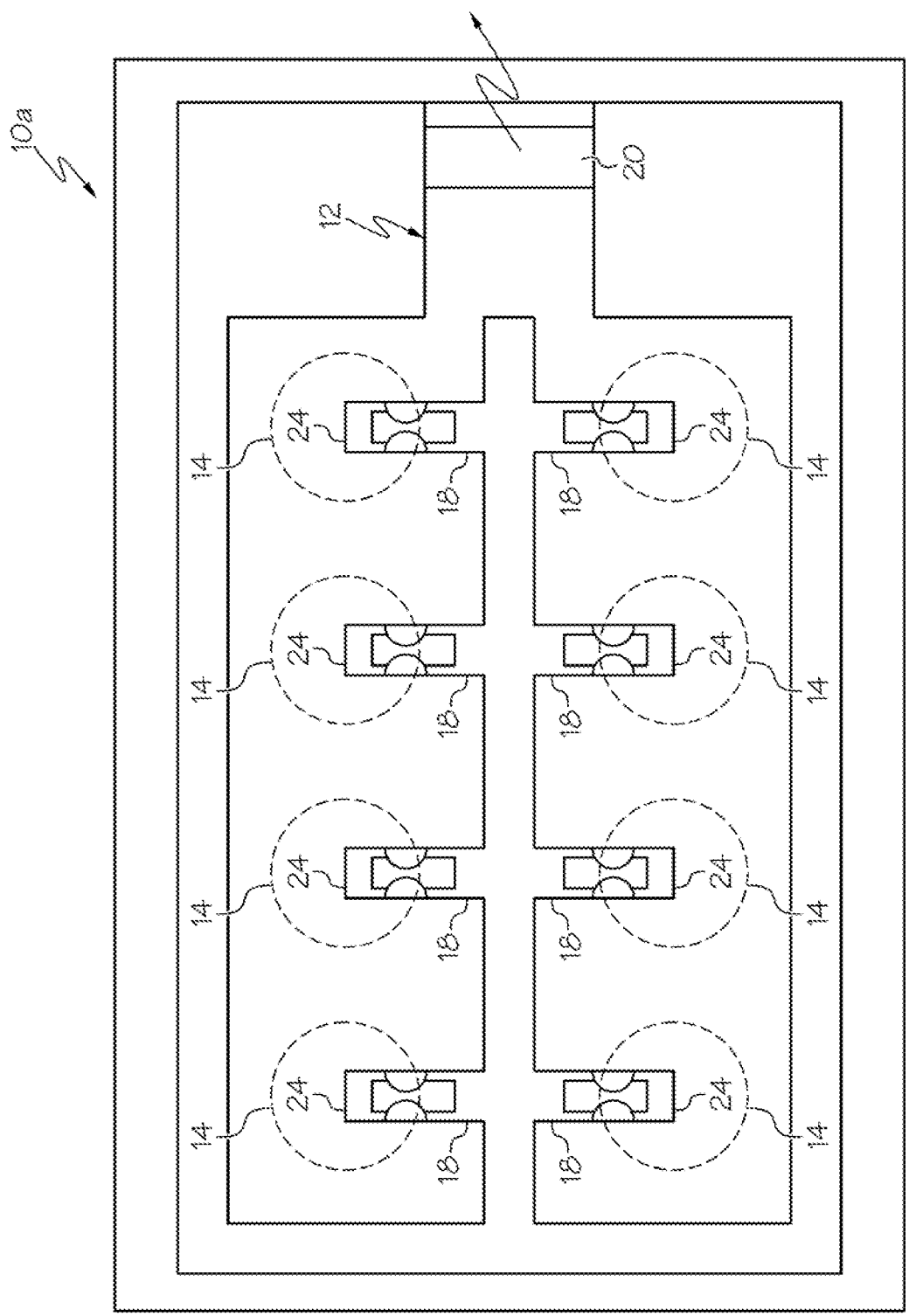
FIG. 2 is a top plan view of another embodiment of a medication container according to an aspect of the present disclosure.
Figure 3:
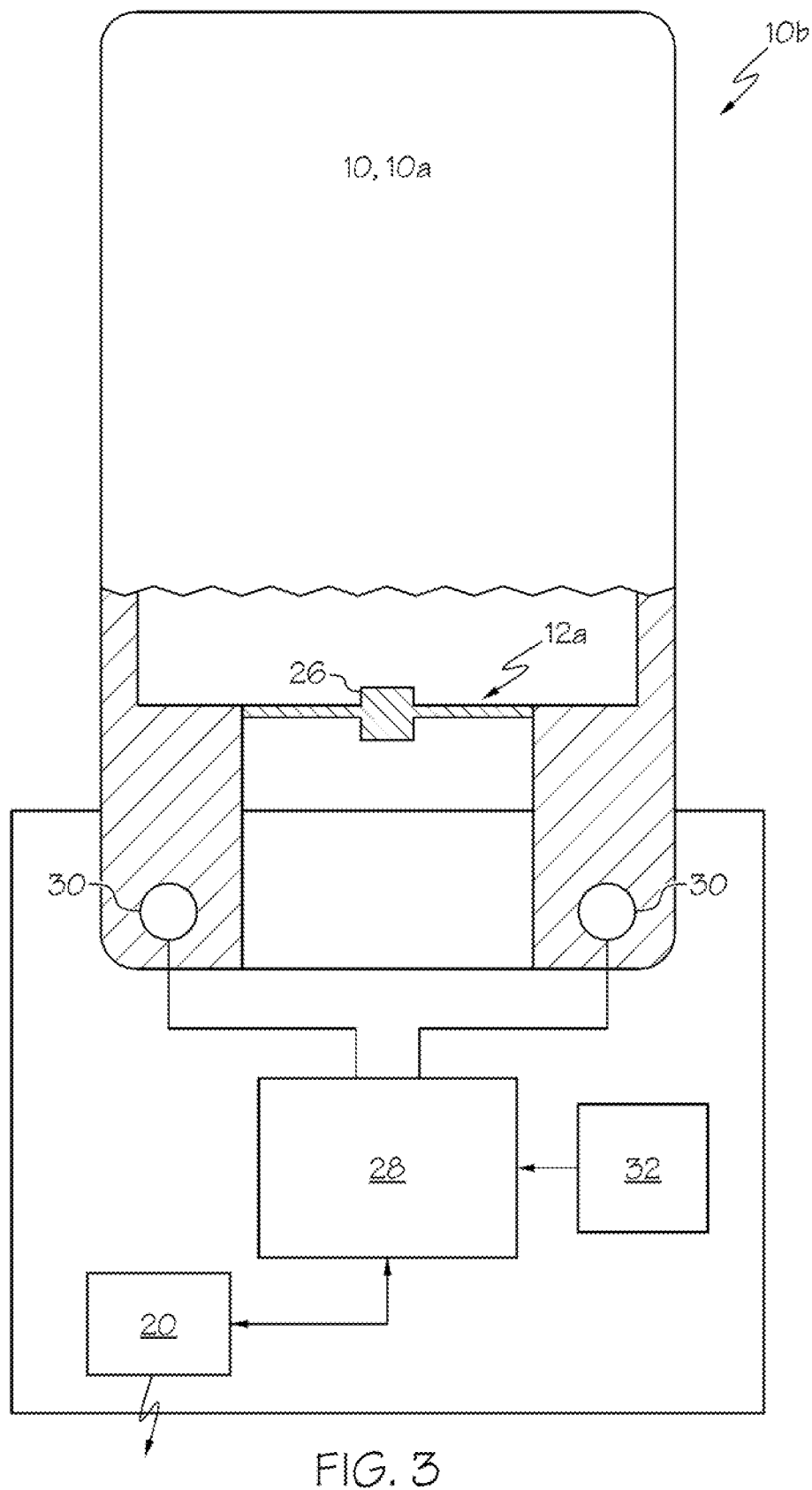
FIG. 3 is a diagrammatic view of yet another embodiment of a medication container according to an aspect of the present disclosure.

According to an aspect of the present disclosure, a doctor or medical care provider may remotely monitor medication compliance through the use of a system that combines an RFID-enabled medication container, generally designated at 10 (FIG. 1) and an RFID reader (not illustrated). An electrical circuit, generally designated at 12, is incorporated into the medication container 10 and configured to allow for the status of a medication-containing cell 14 of the medication container 10 to be monitored to determine whether the cell 14 has been accessed by a subject, in accordance with a prescribed medication routine. FIGS. 2 and 3 illustrate two alternative embodiments of such a system.

Figure 1:
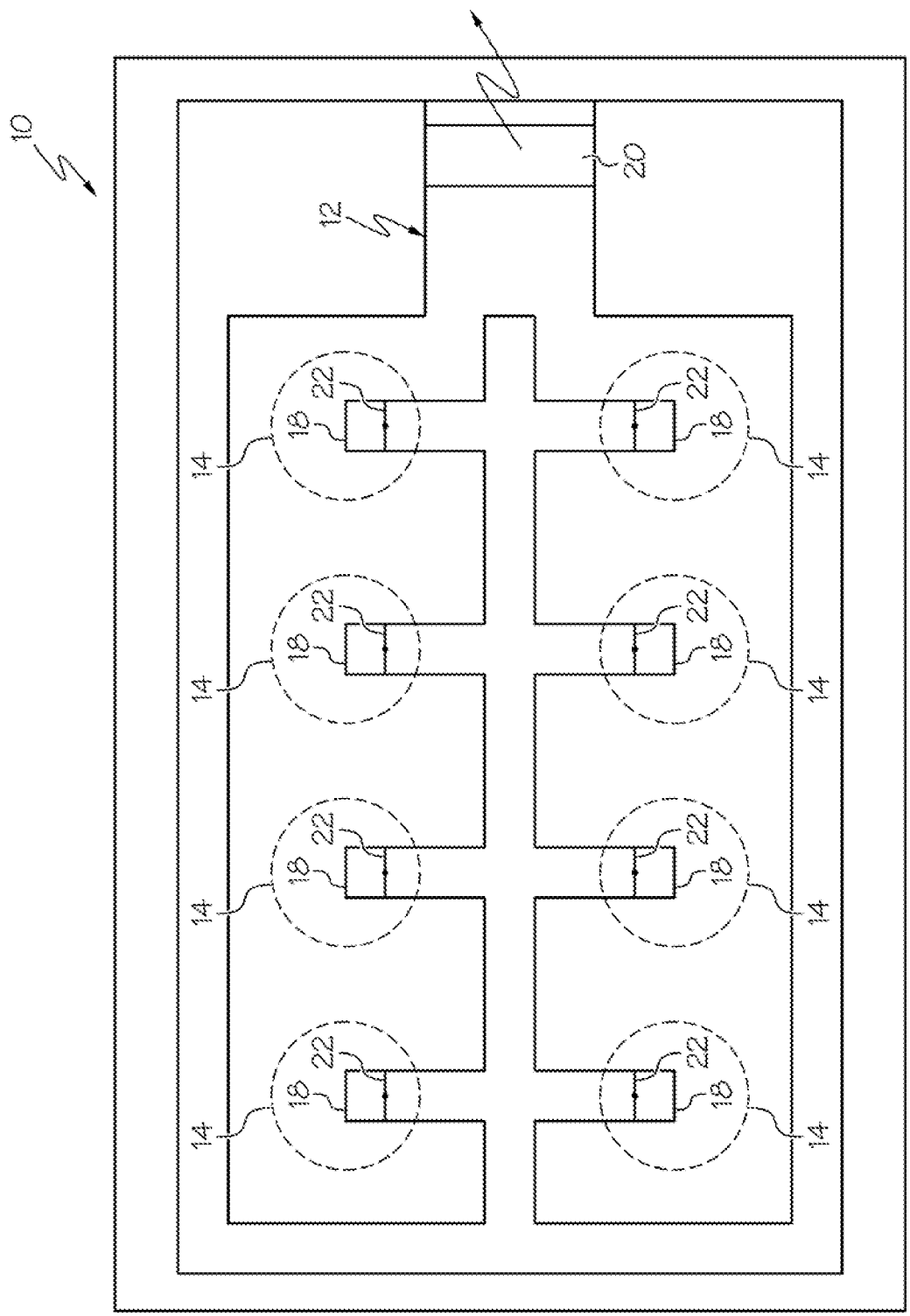
FIG. 1 is a top plan view of a medication container according to an aspect of the present disclosure.

In the embodiment of FIG. 1, the medication container 10 includes at least one cell 14 in which a medication is contained. Preferably, the medication container 10 includes a plurality of identical cells 14 (as in the illustrated embodiment), but it is also within the scope of the present disclosure for a medication container to include only one cell or a plurality of cells differently configured with respect to volume, depth, perimeter size, perimeter shape, color, texture, for example, and combinations thereof.

Each cell 14 may be formed of any suitable material but, in one embodiment, each cell is formed of a plastic material or another material that is substantially non-conductive. It may be advantageous for the cells 14 to be formed of a material that is generally rigid, but sufficiently deformable that a human may deform the individual cells using a finger or digital force and manipulation. In a preferred embodiment, the body of the medical container 10 takes the general form of a blister pack, with a thin plastic sheet being provided with a plurality of chambers that had been formed for containing one medication or multiple medications, such as medications to be accessed and administered at substantially the same time. Each chamber or chambers can be formed as desired. For example, the chamber or chambers can be vacuum-formed depressions or formations that each defines a cell 14 for receiving a dose of medication.

In some instances, it may be thought to be advantageous or efficient for a medication container having a plurality of chambers or cells to be provided from a single sheet that is formed to define all of the chambers or cells It is also within the scope of the present disclosure for the chambers or cells of a single medication container to be separately or non-integrally formed such that less than all of a plurality of the chambers or cells are formed from a formable sheet. This can result in formation of multiple groups or modules having a plurality of chambers or cells grouped in a row or otherwise in general alignment with each other. Each group or module can then assembled into a container of desired size and configuration. Other embodiments may have individual cells formed as separate modules. Chamber or cell formation materials typically comprise polymeric sheeting or cellulosic sheeting or combinations of sheeting materials are selected that can be formed efficiently while providing adequate protection to the contents of each chamber or cell.

Whatever material or configuration is utilized, each chamber or cell 14 is closed or overlaid by a cover 16 through which medication within the cell 14 may be accessed. In one embodiment, the cover 16 is a thin sheet of material, such as a metallic foil, which may be broken to allow a medication to pass out of the chamber or cell 14. In such an embodiment, a base of the cell 14 may be pressed toward the frangible cover 16 by a user until the force on the cover 16 exceeds the strength of the cover 16, at which point the cover 16 breaks and the medication may be removed from the cell 14. Alternatively, the chamber or cell 14 may remain untouched, while the cover 16 is directly engaged and broken by digital force or with simple tool assist in order to remove medication from the cell 14. If the medication container 10 is provided with a plurality of cells 14, it may be preferred for a single cover 16 to overlay all of the cells 14 (as in the illustrated embodiment), but it is also within the scope of the present disclosure for two or more cells of the same medication container to be provided with a common cover, while two or more other cells are provided with a different or separate covers. In another embodiment, different cells are each overlaid by a separate, non-frangible (e.g., hinged) cover.

The electrical circuit 12 incorporated into the medication container 10 includes an RFID chip 18 associated with a chamber or cell 14 and electrically coupled to an antenna 20. The RFID chip 18 may be variously configured without departing from the scope of the present disclosure. For example, in one embodiment, the RFID chip 18 may be of the form defined in the EPC Class1 Gen2 or other protocols that require a bi-directional communication or of the form typically described as "tag talks first", where the RFID chip 18 emits a data burst containing a unique identify at pseudo random intervals when powered. If the medication container 10 includes a plurality of cells 14 (eight in the embodiment of FIG. 1), then it may be advantageous for the circuit 12 to include a plurality of RFID chips 18 (preferably at least as many as the number of chambers or cells 14), with a different RFID chip 18 associated with each one of the cells 14. If a plurality of RFID chips 18 are provided, then they may all be electrically coupled to the antenna 20 in the same way (as shown in FIG. 1). Alternatively, two RFID chips 18 of the same electrical circuit 12 may be electrically coupled to the same antenna 20 in different ways (e.g., with one being electrically coupled to the antenna 20 as in the embodiment of FIG. 1 and another being electrically coupled to the antenna 20 as in the embodiment of FIG. 2, which is described below).

In the illustrated embodiment, each RFID chip 18 is associated with a common antenna 20 by a frangible conductor or link 22. In one embodiment, the frangible conductor or link 22 may be printed onto the cover 16 or otherwise integrated into the cover 16, but it also within the scope of the present disclosure for the frangible conductor or link 22 to be provided separately from the cover 16. The frangible conductor or link 22 is at least partially positioned over the cell 14 associated with the RFID chip 18, such that accessing the medication in the cell 14 (e.g., by breaking or opening the cover 16) breaks the frangible conductor or link 22, thereby uncoupling the associated RFID chip 18 from the antenna 20. For example, the medication may be sealed within the chamber or cell 14, and access can be gained by breaking the cover or otherwise compromising the integrity of the chamber or cell. As will be described in greater detail, the antenna 20 cooperates with an RFID reader to detect when a particular RFID chip 18 is no longer electrically coupled to the antenna 20 (i.e., when the chamber or cell 14 associated with that RFID chip 18 has been accessed).

If the medication container 10 includes a plurality of chambers or cells 14 and RFID chips 18, it may be advantageous for each RFID chip 18 to be programmed with a unique identity, such that when the system determines that an RFID chip 18 has been uncoupled from the antenna 20, it is possible to determine exactly which of the RFID chips 18 has been uncoupled from the antenna 20. Such unique identities may be associated with a particular cell 14 either at the point of use or during manufacture using a map of the position/identity structure.

The antenna 20 may be configured to communicate with an RFID reader at a variety of frequencies, such as high frequency (for detection of the electrical circuit 12 at a relatively short range) or ultra-high frequency (for detection of the electrical circuit 12 at a longer range). In one embodiment, an RFID chip 18 of the electrical circuit 12 is configured to periodically or randomly transmit a signal to the antenna 20 (e.g., a signal indicative of the identity of the RFID chip 18), with the antenna 20 transmitting a signal to the RFID reader to indicate that the frangible link 22 associated with the RFID chip 18 remains intact (i.e., that the chamber or cell 14 associated with the RFID chip 18 has not yet been accessed through or by opening of the cover 16). Alternatively, the RFID reader may be programmed to transmit signals to the antenna 20, at which time the connection between the RFID chip 18 and the antenna 20 is interrogated or checked. If the interrogation reveals that the RFID chip 18 remains electrically coupled to the antenna 20, then the antenna 20 may transmit a signal to the RFID reader that the cell 14 associated with the RFID chip 18 has not yet been accessed through the cover 16. On the other hand, if interrogation reveals that the RFID chip 18 is no longer electrically coupled to the antenna 20, then the antenna 20 may transmit a signal to the RFID reader that the cell 14 associated with the RFID chip 18 has been accessed through the cover 16.

The RFID reader (or a separate electronic device associated or associable with the RFID reader) may include a real-time clock, thereby allowing the system to determine the time (or at least the approximate time) at which the cell 14 associated with a particular RFID chip 18 was accessed through the cover 16. With this information, the system may determine whether a subject is following a prescribed medication routine (i.e., ingesting the proper medication at the proper time) or not (e.g., ingesting an improper medication at a particular time or failing to ingest the proper medication at the prescribed time). In another embodiment (which is described in greater detail herein), the electrical circuit of the medication container may include a real-time clock, thereby allowing a component of the electrical circuit to record the time at which a frangible link 22 was broken (i.e., the time at which a cell 14 associated with the frangible link 22 was accessed through the cover 16). The real time clock device would also have the ability to determine which chip is connected or not, determine a change of that state, and write that data to a permanently connected RFID device such as the master RFID chip to act as the communication medium. This is a fully active circuit, and the real time clock device may monitor the cell connections, determine the connection state, and emulate an RFID tag to send it to the host.

The electrical circuit 12 may include additional components without departing from the scope of the present disclosure. For example, in one embodiment, the electrical circuit 12 includes a motion detector and a power source electrically coupled to the RFID chip(s) 18 and antenna 20. Prior to detecting motion, the electrical circuit 12 may operate in a relatively low power state. Upon the motion detector detecting motion (e.g., when a subject has picked up or moved the medication container 10 to access medication in one of the chambers or cells 14), the electrical circuit 12 may move from the relatively low power state to a relatively high power state, in which the antenna 20 may transmit signals to an RFID reader.

In some embodiments, when the electrical circuit 12 is operating in a relatively high power state, the power is used to increase the operating range of the RFID tags in a way commonly referred to as Battery Assisted Passive, making it possible to read the status of the RFID chips at either longer range or with a lower power reader device.

In an alternative embodiment, the RFID chips may be inhibited from communication with a reader system when in low power state and enabled in the high power state. This is useful as it ensures that only RFID devices associated with a moving blister pack are active, reducing the number of parts attempting to communicate with the reader, when a relatively large number of blister packs are present. At any suitable time (e.g., after a certain amount of time during which the motion detector fails to detect motion), the electrical circuit 12 may move back into the relatively low power state from the relatively high power state. The configuration of the motion detector and power source may vary without departing from the scope of the present disclosure. For example, in one embodiment, the motion detector may be provided as a passive infrared device, which operates based on the presumption that medication will only be removed from a cell 14 when a human is present.

In another embodiment, the electrical circuit 12 may be provided with a second antenna, which allows the electrical circuit 12 to be interrogated at a second or alternative frequency. The second antenna may take any suitable form (e.g., a coil for receiving magnetic field signals or capacitive pads for receiving electric field signals) and be variously associated with the medication container 10 without departing from the scope of the present disclosure.

The RFID reader of the system also may be provided with any of a variety of components and functionality without departing from the scope of the present disclosure. For example, the RFID reader may have its own wide area communication capability, such as via WiFi, 3G, or 4G, or may communicate via another linking system, such as Bluetooth, to a smart device such as a mobile phone or tablet or the like.

As described above, in the embodiment of FIG. 1, an RFID chip 18 is configured to be uncoupled from the antenna 20 upon the associated chamber or cell 14 being accessed through the cover 16. An alternative embodiment of a medication container, generally designated as 10a, is illustrated in FIG. 2. In this embodiment, the RFID chip 18 remains electrically coupled to the antenna 20 after the associated cell 14 has been accessed through the cover 16. In this embodiment, each RFID chip 18 is provided with an associated anti-tamper chip 24 (e.g., a G2iL+ device from NXP Semiconductors of Eindhoven, The Netherlands). When the cell 14 associated with the anti-tamper chip 24 is accessed (e.g., by breaking the cover 16 overlaying the cell 14), the state of the anti-tamper chip 24 changes, which changes a bit in memory, which is indicative of the cell 14 having been accessed through the cover 16. This change will affect the signal received by the antenna 20 from the RFID chip 18 associated with the anti-tamper chip 24, which affects the signal that the antenna 20 transmits to an RFID reader of the system. The RFID reader (or another component of the system) may be configured or programmed to recognize that the different signal from the antenna 20 indicates that one of the cells 14 has been accessed, typically being through the cover 16.

Another difference between the embodiment illustrated in FIG. 1 and that illustrated in FIG. 2 is the way in which the respective RFID chips 18 are incorporated into the respective medication container 10, 10a. In the embodiment of FIG. 1, a greater amount of foil is illustrated than in FIG. 2. In FIG. 1, the substantially complete layer of foil may comprise at least a portion of the cover 16 (along with a support layer formed of paper or the like, optionally), with laser-formed gaps being defined at selected locations of the foil. Each RFID chip 18 is installed across the gap in the foil by a "flip chip" method or the like to associate the RFID chips 18 with the medication container 10. In contrast, the RFID chips 18 of the embodiment of FIG. 2 are incorporated into the associated medication container 10a according to a suitable alternative approach. It should be understood, however, that the RFID chip-connection approach of FIG. 1 may be used to connect the RFID chips 18 of FIG. 2, as well as for the RFID chips 18 of FIG. 1 to be connected by an approach other than a "flip chip" method.

FIG. 3 illustrates another embodiment of a medication container, generally designated at 10b, according to the present disclosure. The medication container 10b of FIG. 3 may be provided according to the above description of either embodiment of FIGS. 1 and 2 (indicated generally at 10, 10a in FIG. 3), but with additional components incorporated into the electrical circuit, generally designated at 12a. The various components illustrated in FIG. 3 and described below may be practiced in any combination or individually without departing from the scope of the present disclosure.

In the embodiment illustrated in FIG. 3, the electrical circuit 12a is provided with a master RFID chip 26 electrically coupled to the antenna 20. In contrast to the RFID chips 18 of FIGS. 1 and 2, the master RFID chip 26 is not associated with any particular chamber or cell 14, but instead with the medication container 10b itself. Also in contrast to the embodiments of FIG. 1, the master RFID chip 26 is configured to remain coupled to the antenna 20 during use, rather than ever becoming uncoupled from the antenna 20. The master RFID chip 26 may be programmed with data indicative of the identity of the medication container 10b, such that an RFID reader (either the same one that monitors the status of the individual cells or a different RFID reader) may track the medication container 10b as part of an inventory management system or the like (typically at ultra-high frequency to track the medication container 10b in a relatively large read field). The master RFID chip 26 may even allow for the medication container 10b to be monitored following use without having to physically contact the medication container 10b, provided that the medication container 10b is not disposed of in a receptacle that interferes with signals to and/or from the antenna 20 (e.g., a metallic disposal container). A reader system may, upon determining which RFID chips are coupled to the common antenna as well as the master chip 26, write to master chip 26 a data set containing the time at which chips were present at that time, The data set may only be written when there is a change of the state of which chips are connected, The data set stored in master chip 26 may be retrieved via a reader at a later time to allow post use analysis, although this is considered of lower value than real time monitoring.

The electrical circuit 12 of FIG. 3 is further provided with a microcontroller or low power reader/writer device 28, which is electrically coupled to the medication container 10b by any suitable means (e.g., by capacitive contact via two large pads 30 or by an RF signal in a near or far field). In a particular embodiment, which is illustrated in FIG. 3, the reliability of the connection between the microcontroller 28 and the medication container 10b is greatly enhanced by having a small number of large connections. The connection may carry a signal at ultra-high frequency or at a lower frequency. For example, the clock of the microcontroller 28 executing a read/write operation; typical frequencies for the connection would be in the range of 4 MHz to 32 MHz, although lower or higher frequencies may be used. Some RFID chips 18 of the electrical circuit 12 of the medication container 10b, specifically those without internal coupling capacitors, may be interrogated using data signals at the supply voltage of the microcontroller 28.

The microcontroller 28 may be programmed to register and record a change in the structure of the electrical circuit 12 (corresponding to one of the cells 14 of the medication container 10b being accessed through the cover 16). If the medication container 10b includes a plurality of chambers or cells 14, the microcontroller 28 may separately monitor the status of each chamber or cell 14 and distinguish them based on the identity of the associated RFID chip 18 and the unique signal transmitted by the associated RFID chip 18. In the illustrated embodiment, a real-time clock 32 is electrically coupled to the microcontroller 28, which allows the microcontroller 28 to register and record the time at which a particular cell 14 of the medication container 10b was accessed through the cover 16. Alternatively, rather than storing this information itself, the microcontroller 28 may be programmed to write the information into a separate storage location (e.g., an RFID chip of the electrical circuit 12). By storing information about the use of the medication container 10b, the microcontroller 28 allows for all of the information to be accessed by an RFID reader with fewer interactions (e.g., a single interaction) between the RFID reader and the electrical circuit 12 of the medication container 10b.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A medication container, comprising:
    at least one medication-containing cell;
    a cover overlaying the cell through which medication contained within the cell is to be accessed; and
    an electrical circuit including
        at least one RFID chip, each RFID chip being associated with the cover and having a unique identity that is associated with a corresponding one of the at least one medication-containing cell,
        a master RFID chip associated with the medication container, and distinct from the at least one RFID chip on the cover,
        an antenna electrically coupled to the at least one RFID chip and configured to communicate with an RFID reader to detect whether the at least one medication-containing cell has been accessed through the cover, and the at least one RFID chip is associated with the antenna by a frangible conductor;
    a power source; and
    a motion detector having a passive infrared device electrically coupled to the at least one RFID chip and the antenna, wherein the electrical circuit is configured to operate in a first power state before the motion detector detects motion and to operate in a second power state after the motion detector detects motion, where the at least one RFID chip has a first read range when the electrical circuit operates in the first power state and a second read range when the electrical circuit operates in the second power state.

2. The medication container of claim 1, configured as a blister pack.

3. The medication container of claim 1, wherein the at least one RFID chip is associated with the at least one medication-containing cell such that accessing the at least one medication-containing cell through the cover uncouples the at least one RFID chip from the antenna.

4. The medication container of claim 1, wherein the at least one RFID chip is associated with the at least one medication-containing cell such that accessing the at least one medication-containing cell through the cover does not uncouple the at least one RFID chip from the antenna.

5. The medication container of claim 4, wherein the electrical circuit further includes at least one anti-tamper chip, each anti-tamper chip electrically coupled to a corresponding one of the at least one RFID chip and the antenna, the anti-tamper chip being configured to indicate whether the at least one medication-containing cell has been accessed through the cover.

6. The medication container of claim 1, further comprising a plurality of medication-containing cells and a plurality of RFID chips, wherein
    the cover overlays each of the cells,
    each RFID chip is associated with a different one of said cells, and
    each RFID chip is electrically coupled to the antenna and configured to indicate whether the associated cell has been accessed through the cover.

7. The medication container of claim 6, wherein all of the RFID chips are electrically coupled to the antenna in the same way.

8. The medication container of claim 6, wherein at least two of the RFID chips are electrically coupled to the antenna in different ways.

9. The medication container of claim 1, wherein the antenna is configured to communicate with the RFID reader at high frequency.

10. The medication container of claim 1, wherein the antenna is configured to communicate with the RFID reader at ultra-high frequency.

11. The medication container of claim 1, wherein the electrical circuit further includes a microprocessor electrically coupled to the antenna.

12. The medication container of claim 11, wherein the electrical circuit further includes a real-time clock electrically coupled to the microprocessor.

13. The medication container of claim 12, wherein the microprocessor is programmed to determine and record the time at which the RFID chip becomes uncoupled from the antenna.

14. The medication container of claim 1, wherein the master RFID chip is electrically coupled to the antenna.

15. The medication container of claim 14, wherein the master RFID chip is configured to remain coupled to the antenna during use of the medication container.

16. The medication container of claim 14, wherein the master RFID chip is programmed with data indicative of the identity of the medication container.

17. The medication container of claim 1, wherein the at least one RFID chip is programmed to periodically transmit a signal to the antenna while the at least one RFID chip is electrically coupled to the antenna.

18. The medication container of claim 1, wherein the at least one RFID chip is programmed to transmit a signal to the antenna only upon receiving a signal from the RFID reader.

19. A medication container, comprising:
   at least one medication-containing cell;
   a cover overlaying the at least one medication-containing cell through which medication contained within the at least one medication-containing cell is to be accessed; and
   an electrical circuit including
      an RFID master chip associated with the medication container that is programmed with data indicative of an identity of the medication container,
      at least one RFID chip associated with the at least one medication-containing cell,
      a microcontroller electrically coupled to the medication container,
      a real-time clock electrically coupled to the microcontroller,
      a first antenna electrically coupled to the at least one RFID chip and configured to communicate with an RFID reader to detect whether the at least one medication-containing cell has been accessed through the cover and the microcontroller is programmed to determine and record the time at which the RFID chip becomes uncoupled from the first antenna, and programmed to write the information into a separate storage location, the first antenna further coupled to the RFID master chip, the RFID master chip configured to store a data set written by the RFID reader,
      a power source,
      a second antenna that allows the electrical circuit to be interrogated at an alternative frequency, and
      a motion detector electrically coupled to the at least one RFID chip and the first antenna, where the electrical circuit is configured to operate in a relatively low power state before the motion detector detects motion and to operate in a relatively high power state after the motion detector detects motion.

20. The medication container as provided in claim 19, wherein the data set contains time at which the RFID chip is present.

21. The medication container as provided in claim 19, wherein the data set is written to when a change of state of the RFID chip is detected.

22. The medication container as provided in claim 20, wherein the data set stored in the RFID master chip is retrieved via the RFID reader for use analysis of the medication container.

* * * * *